US00PP30638P2

(12) United States Plant Patent
Winslow

(10) Patent No.: US PP30,638 P2
(45) Date of Patent: Jul. 2, 2019

(54) ***IPOMOEA* PLANT NAMED 'BALSOLAREDAR'**

(50) Latin Name: *Ipomoea batatas*
Varietal Denomination: Balsolaredar

(71) Applicant: Ball Horticultural Company, West Chicago, IL (US)

(72) Inventor: Benjamin K. Winslow, Austin, TX (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/932,575

(22) Filed: Mar. 16, 2018

(51) Int. Cl.
*A01H 5/12* (2018.01)

(52) U.S. Cl.
USPC ..... Plt./258

(58) Field of Classification Search
USPC ..... Plt./258
CPC ... A01H 5/12; A01H 5/06; A01H 5/02; A01H 5/04; A01H 5/00; A01H 6/00
See application file for complete search history.

*Primary Examiner* — June Hwu
(74) *Attorney, Agent, or Firm* — Audrey Charles

(57) ABSTRACT

A new and distinct cultivar of an ornamental *Ipomoea* plant named 'Balsolaredar', characterized by its heart-shaped, dark bronzed-burgundy colored foliage, and moderately vigorous, mounded-spreading growth habit, is disclosed.

1 Drawing Sheet

Latin name of genus and species of plant claimed: *Ipomoea batatas*.
Variety denomination: 'Balsolaredar'.

BACKGROUND OF THE INVENTION

The present invention relates to a new and distinct cultivar of *Ipomoea* plant botanically known as *Ipomoea batatas* and hereinafter referred to by the cultivar name 'Balsolaredar'.

The new cultivar originated in a controlled breeding program in Arroyo Grande, Calif. during October 2012. The objective of the breeding program was the development of ornamental *Ipomoea* cultivars with heart-shaped leaves and a moderately vigorous, mounded-spreading habit.

The new ornamental *Ipomoea* cultivar is the result of cross-pollination. The female (seed) parent of the new cultivar 'Sweet Caroline Bronze', U.S. Plant Pat. No. 15,437, characterized by its bronze to purple-bronze colored foliage and compact-mounded-spreading growth habit. The male (pollen) parent of the new cultivar is ILLUSION Garnet Lace 'NCORNSP-013GNLC', U.S. Plant Pat. No. 23,612, characterized by its burgundy-red colored foliage and compact, semi-upright, mounded-spreading growth habit. The new cultivar was discovered and selected as a single plant within the progeny of the above stated cross-pollination during April 2015 in a controlled environment in Arroyo Grande, Calif.

Asexual reproduction of the new cultivar by terminal stem cuttings since April 2015 in Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsolaredar' as a new and distinct cultivar of *Ipomoea* plant:

1. Heart-shaped, dark bronzed-burgundy colored foliage; and
2. Moderately vigorous, mounded-spreading growth habit.

Plants of the new cultivar differ from plants of the female and male parents primarily in having heart-shaped foliage and a different foliage color.

Of the many commercially available ornamental *Ipomoea* cultivars, the most similar in comparison to the new cultivar is SolarPower Red 'Balsolared', U.S. Plant Pat. No. 26,686. However, in comparison, plants of the new cultivar differ from plants of 'Balsolared' in at least the following characteristics:

1. Plants of the new cultivar have heart-shaped foliage unlike plants of 'Balsolared'; and
2. Plants of the new cultivar has more branches than plants of 'Balsolared'.

BRIEF DESCRIPTION OF THE PHOTOGRAPHS

The accompanying photographs show, as nearly true as it is reasonably possible to make the same in color illustrations of this type, typical foliage characteristics of the new cultivar. Colors in the photographs differ slightly from the color values cited in the detailed description, which accurately describes the colors of 'Balsolaredar'. The plants were grown in 4-inch pots for 9 weeks in a greenhouse in West Chicago, Ill.

DETAILED BOTANICAL DESCRIPTION

Figure 1:
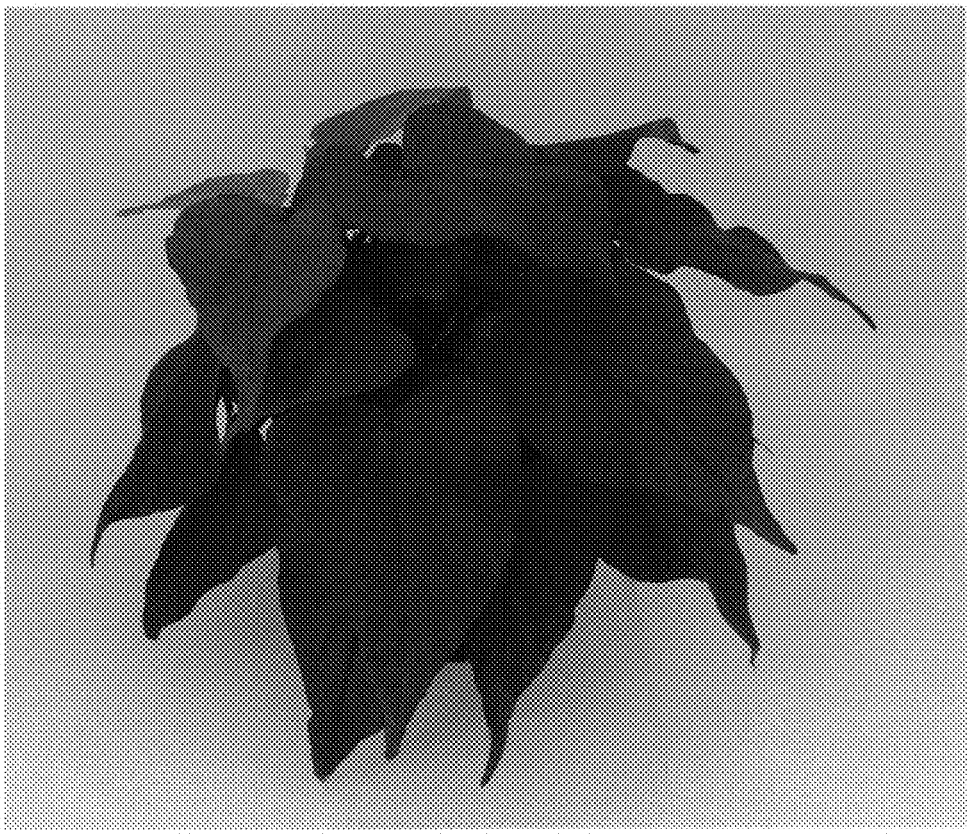
FIG. 1 illustrates a side view of the overall growth and habit of 'Balsolaredar'.
Figure 2:
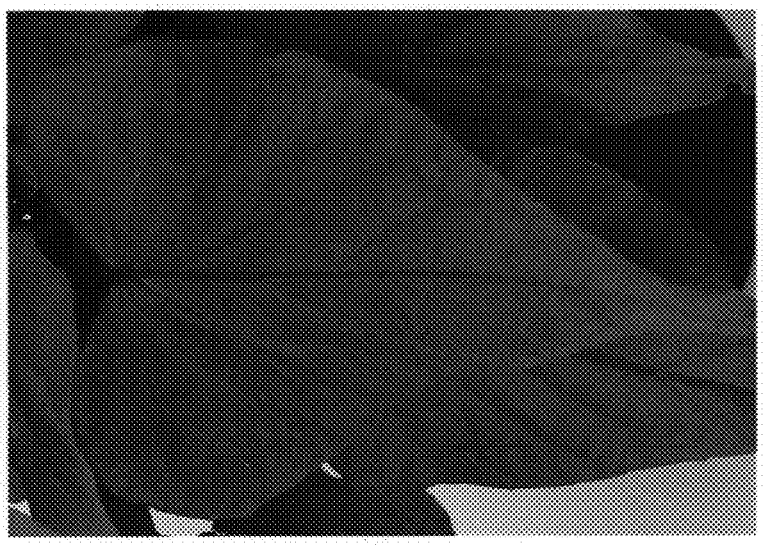
FIG. 2 illustrates a close-up view of an individual leaf of 'Balsolaredar'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2018 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 10 weeks in a greenhouse utilizing a soilless growth medium. Greenhouse temperatures were maintained at approximately 68° F. to 72° F. (20° C. to 22° C.) during the day and approximately 64° F. to 66° F. (18° C. to 19° C.) during the night. Supplemental lighting was used. Measurements and numerical values represent averages of typical plants.

Botanical classification: *Ipomoea batatas* 'Balsolaredar'.

Parentage:

*Female parent*.—'Sweet Caroline Bronze', U.S. Plant Pat. No. 15,437.

*Male parent*.—ILLUSION Garnet Lace 'NCORNSP-013GNLC', U.S. Plant Pat. No. 23,612.

Propagation:

*Type cutting*.—Terminal stem.

*Time to initiate roots*.—Approximately 3 to 4 days.

*Time to produce a rooted cutting*.—Approximately 21 to 28 days.

*Root description*.—Fibrous, medium thickness.

*Rooting habit*.—Freely branching.

*Tuber description*.—Not available, tuber formation not observed to date.

Plant description:

*Commercial crop time*.—Approximately 4 to 5 weeks from a rooted cutting to finish in a 10 cm pot.

*Growth habit and general appearance*.—Moderately vigorous, mounded- spreading.

*Size*.—Height: Approximately 12.0 cm. Width: Approximately 28.0 cm.

*Branching habit*.—Freely branching, pinching enhances basal branching. Quantity of main lateral branches per plant: Approximately 8.

*Branch*.—Shape: Round. Strength: Strong, slightly flexible. Length: Approximately 3.5 cm. Diameter: Approximately 4.0 mm. Length of central internode: Approximately 5.0 mm. Texture of young stems: Sparsely pubescent. Texture of mature stems: Glabrous. Color of young stems: 145C with an overlay of 187B. Color of mature stems: 187A.

Foliage description:

*General description*.—Quantity of leaves per main branch: Approximately 6. Fragrance: None detected. Form: Simple. Arrangement: Alternate, spiral.

*Leaves*.—Shape: Cordate. Margin: Entire. Apex: Broadly acuminate to broadly acute. Base: Cordate. Venation pattern: Palmate. Length of mature leaf: Approximately 11.0 cm. Width of mature leaf: Approximately 9.0 cm. Texture of upper and lower surfaces: Glabrous. Color of upper surface of young foliage: 145A with an overlay of 187B, venation of 187B to same color as lamina. Color of lower surface of young foliage: Closest to 146D with a faint overlay of 187B, venation same color as lamina with midvein base of 187B. Color of upper surface of mature foliage: Closest to NN137A mixed with 187B having an overall bronzed-burgundy appearance, venation of N186C. Color of lower surface of mature foliage: Closest to but more greyish purple than N186D, venation of N186D.

*Petiole*.—Length: Approximately 7.3 cm. Diameter: Approximately 3.0 mm. Texture: Glabrous. Color: 187B.

Flowering description: Not available, flower and seed formation not observed to date. The new ornamental *Ipomoea* cultivar is grown as a foliage plant and is not grown under conditions that are conducive to flower production.

Disease and pest resistance: Resistance to pathogens and pests common to *Ipomoea* has not been observed.

What is claimed is:

1. A new and distinct cultivar of an ornamental *Ipomoea* plant named 'Balsolaredar', substantially as herein illustrated and described.

* * * * *